(12) United States Patent
Lees (10) Patent No.: US 7,857,271 B2
(45) Date of Patent: Dec. 28, 2010

(54) SURGICAL TOOL HOLDER WITH ENGAGEMENT PORTIONS

(75) Inventor: John Lees, Richmond, VA (US)

(73) Assignee: Automated Medical Products Corporation, Sewaren, NJ (US)

( * ) Notice: Subject to any disclaimer, the term of this patent is extended or adjusted under 35 U.S.C. 154(b) by 648 days.

(21) Appl. No.: 11/165,064

(22) Filed: Jun. 24, 2005

(65) Prior Publication Data

US 2006/0290076 A1 Dec. 28, 2006

(51) Int. Cl.
*E04G 3/00* (2006.01)
(52) U.S. Cl. .............. 248/286.1; 248/287.1; 248/296.1; 248/284.1; 248/295.11; 248/292.12; 248/298.1; 5/648; 600/201; 602/32; 602/33; 602/35; 602/36
(58) Field of Classification Search .............. 248/286.1, 248/287.1, 296.1, 284.1, 295.11, 292.12, 248/298.1; 5/648; 600/201; 602/32, 33, 602/35, 36
See application file for complete search history.

(56) References Cited

U.S. PATENT DOCUMENTS

| | | | | |
|---|---|---|---|---|
| 1,451,881 A | * | 4/1923 | McMullen ............... 248/230.5 |
| 3,046,072 A | * | 7/1962 | Douglass, Jr. et al. .......... 5/646 |
| 3,267,202 A | * | 8/1966 | Leonard .................... 174/45 R |
| 3,339,913 A | | 9/1967 | Anderson .................... 269/328 |
| 3,417,953 A | * | 12/1968 | Hillquist et al. .......... 248/284.1 |
| 4,143,652 A | * | 3/1979 | Meier et al. .................. 600/203 |
| 4,547,092 A | * | 10/1985 | Vetter et al. .................... 403/59 |
| 4,796,846 A | | 1/1989 | Meier et al. ................. 248/286 |
| 5,116,008 A | * | 5/1992 | Allen ....................... 248/286.1 |
| 5,135,210 A | * | 8/1992 | Michelson ..................... 5/658 |
| 5,538,215 A | | 7/1996 | Hosey ..................... 248/246.1 |
| 6,315,260 B1 | | 11/2001 | Lees ....................... 248/286.1 |
| 6,598,275 B1 | | 7/2003 | Kolody et al. ................. 24/455 |
| 6,622,980 B2 | * | 9/2003 | Boucher et al. ........ 248/231.51 |
| 6,691,350 B2 | * | 2/2004 | Weismiller ..................... 5/621 |
| 2004/0144905 A1 | * | 7/2004 | Ropertz et al. ........... 248/286.1 |

* cited by examiner

Primary Examiner—Anita M King
Assistant Examiner—Nkeisha J Smith
(74) Attorney, Agent, or Firm—Dorsey & Whitney, LLP.

(57) ABSTRACT

A surgical tool holder that includes a holding member with a clamping jaw, which is movable between open and clamping positions. A gripping member is configured to supportingly grip a surgical tool and is selectively placed in a rotatable or fixed association with the holding member. Engagement portions of the holding member and gripping member are engagable to block rotation therebetween to obtain the fixed association.

18 Claims, 5 Drawing Sheets

SURGICAL TOOL HOLDER WITH ENGAGEMENT PORTIONS

FIELD OF THE INVENTION

The present invention relates to a surgical tool holder, and more particularly to a surgical tool holder with engagement portions for blocking rotation between components of the holder.

BACKGROUND OF THE INVENTION

Swinger clamps, such as disclosed in U.S. Pat. Nos. 4,796,846 and 6,315,260, are used to support surgical tools during surgical procedures. These types of devices are often used to support a rib grip, or other retractors or devices, often in abdominal surgery.

Typically, a swinger clamp is clamped onto a rail guide, and a vertical bar is inserted into and held by the swinger clamp. The support bar can support, either directly or via another bar attached thereto, one or more surgical devices. For example, during a liver transplant, the ribcage and stomach are often held in a retracted position to provide access to the surgery site. The bar is typically positioned at the desired angle, and the swinger clamp is tightened to support the bar in a desired position. Between uses, the known devices are autoclaved and the surfaces should be cleaned to remove any debris.

Since the movable parts of the known swinger clamps typically retain a fixed position and association with respect to each other by friction, the relative fixation between these parts is affected by surface contamination. Particulate residue and other debris, for example, can significantly decrease the friction between these parts causing undesired slippage even when the residue is sterile. The frictional engagement is especially susceptible when used in surgery on morbidly obese patients, where the forces the clamp is subjected to are especially high.

A swinger clamp or a tool holder is thus needed with improved tolerance for sterilized surface contamination in the event the device is not thoroughly cleaned of debris in conjunction with conventional sterilization, e.g., autoclaving.

SUMMARY OF THE INVENTION

The present invention relates to a surgical tool holder, such as a three-dimensional swinger clamp. In a preferred embodiment, the tool holder includes a holding member, such as a holder block, that includes a clamping jaw. The clamping jaw is movable between an open position, for receiving a guide rail, and a clamping position, for clamping the guide rail to mount the holding member to a guide rail. The holding member also preferably includes a first engagement portion. A gripping member of the tool holder is configured for supportingly gripping a surgical tool. The gripping member has a rotatable association with the holding member, in which it is rotatable with respect thereto, as well as a fixed association with the holding member when the jaw is in the clamping position. The gripping member includes a second engagement portion that is configured to abut the first engagement portion in an engaged association that substantially blocks rotation between the holding member and the gripping member. Preferably, the engagement portions are engaged when the gripping and holding members are in the fixed association, and the engagement portions substantially or entirely do not rely on friction to limit and arrest rotational movement of the holding and gripping members.

The first and second engagement portions are preferably configured to mesh with each other in the engaged association and most preferably include a plurality of intermeshable teeth on at least one, and preferably on both, of the engagement portions. The preferred second engagement portion extends circumferentially around the holding member for engagement with the first engagement portion in a plurality of relative rotational positions therebetween. Also, in the preferred embodiment, the first engagement portion is provided on the jaw of the holding member.

In this embodiment, the holding and gripping members are rotatable about a first axis, in the rotatable association, when the engagement portions are disengaged. The first and second holders can be configured for allowing the jaw to pivot about a second axis that is oriented at an angle to, and is preferably displaced from, the first axis to release and capture the guide rail, while maintaining the engagement portions in the engaged association to block relative rotation between the holding and gripping members about the first axis.

Preferably, the jaw includes a contact surface that includes the first engagement portion. The contact surface can be curved to maintain the engaged association of the holders throughout the rotation of the jaw about the second axis. The preferred jaw is resiliently biased to pivot away from the clamping position about the second axis and is configured to cam the second engagement portion away from the holding member under this bias. The jaw can be pivotable to disengage the engagement portions from each other.

An actuating member can be operably associated with the holding and gripping members to reversibly move the jaw to the clamping position and cause the gripping member to grip the surgical tool. The actuating member preferably moves the jaw to the clamping position and causes the gripping member to grip the surgical tool substantially simultaneously and in a single operation. The operation of the actuating member can consequently cause the second engagement portion to cam the first engagement portion towards the clamping position. The preferred actuating member is in pivotal association with the holding member to compress the gripping portion against the jaw to tighten the clamping of the jaw and the gripping of the gripping member.

The present invention thus can advantageously provide a versatile surgical tool holder with improved resistance to rotation between the components thereof even when the engaging surfaces are not completely free of sterilized debris or even other contaminants.

BRIEF DESCRIPTION OF THE DRAWINGS

Further features and advantages of the invention can be ascertained from the following detailed description that is provided in connection with the illustrative drawing(s) of a preferred embodiment described below.

DETAILED DESCRIPTION OF THE PREFERRED EMBODIMENTS

The advantages of the present invention can be readily described when considering conventional swinger clamps, such as those disclosed in U.S. Pat. Nos. 4,796,846 and 6,315,260, the entire contents of each of which is expressly incorporated herein by reference thereto.

Figure 1:
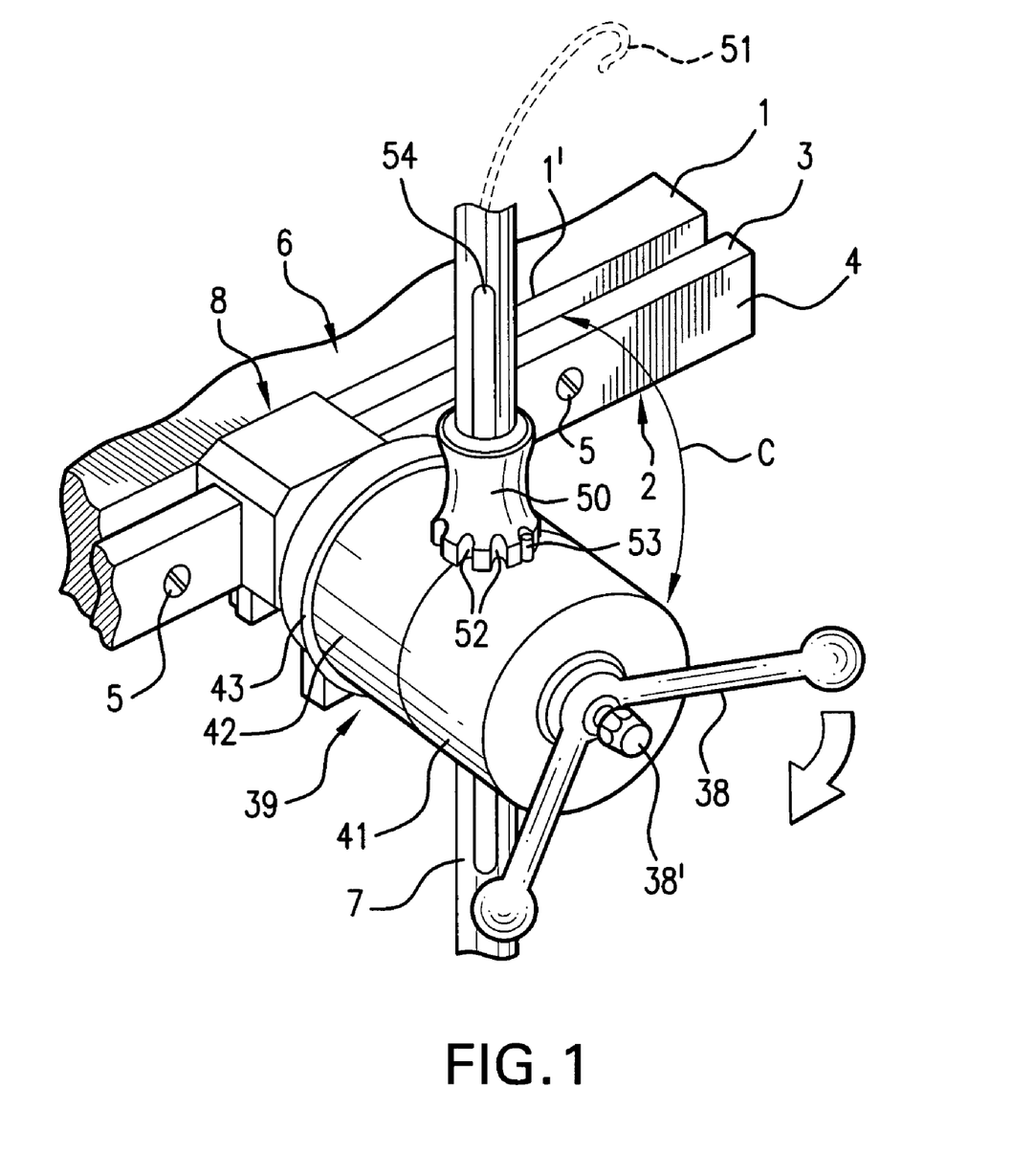
FIG. 1 is a perspective view of a preferred embodiment of a surgical tool holder constructed according to the present invention.
Figure 1A:
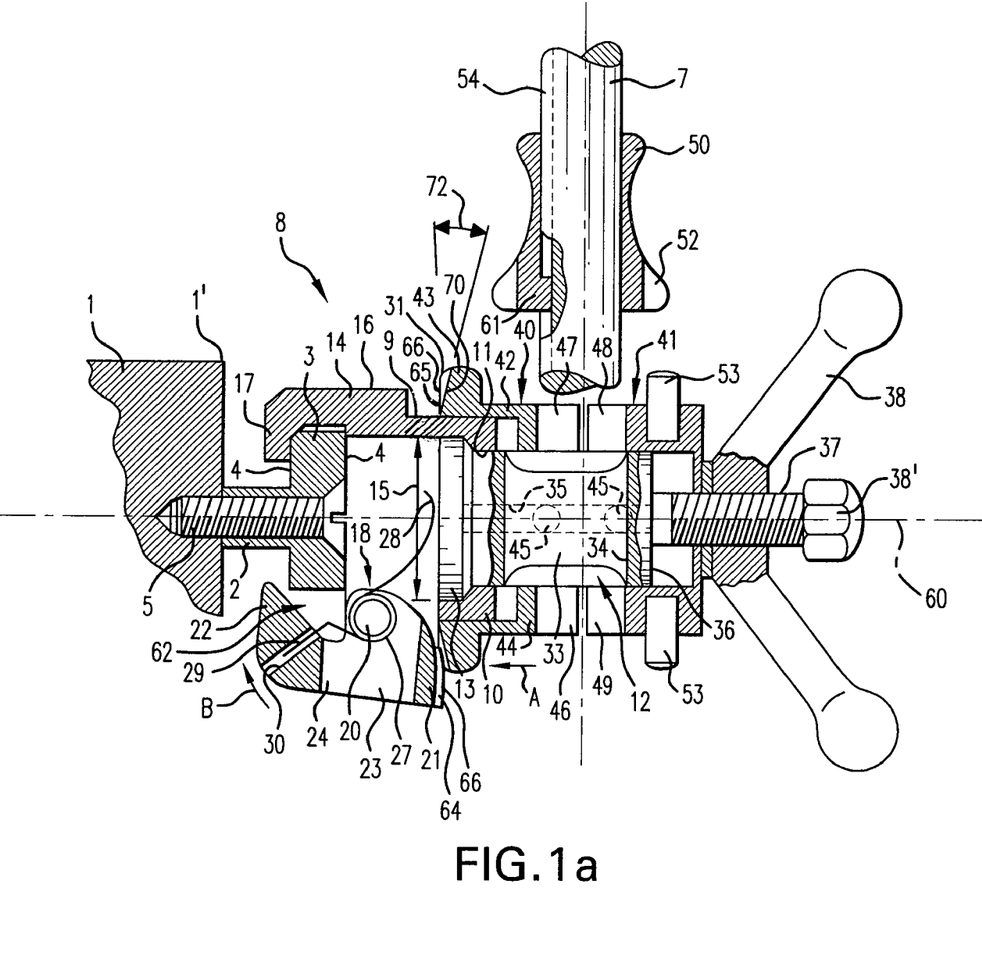
FIG. 1a is a cross-sectional view thereof according to the present invention.

With reference to FIGS. 1 and 1a, a preferred embodiment of a surgical tool holding or retaining device 6 includes a holding member, including a holder block 8, and a clamping or gripping mechanism 39. The holder block 8 is selectively displaceably mountable and fixable to a guide rail 2, for example, to secure the device 6 along a longitudinal edge or side 1' of an operating table 1 from which the guard rail 2 extends. The guide rail 2 preferably has a substantially T-shaped cross-section, with a narrow horizontal face or surface 3 and vertical faces or surfaces 4, although any other configurations available to those of ordinary skill in the art can be used. The guide rail 2 of this embodiment is fixedly connected to the longitudinal edge 1' of the operating table 1, for example, by screws 5 spaced along the length of the guide rail 2 or another type of fastener.

The device 6 is selectively displaceable along, and fixable in different positions to, the guide rail 2 and also serves to receive and positively hold one or more surgical tools, such as an instrument support, for example a support rod 7 or other surgical supporting member. The position of the support rod 7 can be adjusted and positively locked in different elevational and angular positions in the device 6. The support rod 7 is configured to hold one or more surgical instruments 51, including, but not limited to, a wound hook, retractor, specular, wound spreader, magnifying lens, spatula, or X-ray plate holder or cassette, or any combination thereof. This support rod 7 can comprise interlinked or articulated members, as known in the art.

Figure 4:
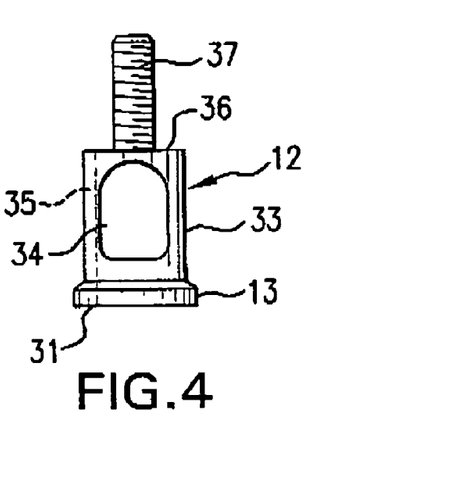
FIG. 4 is a front view of a thrust sleeve of the preferred embodiment according to the present invention.
Figure 5:
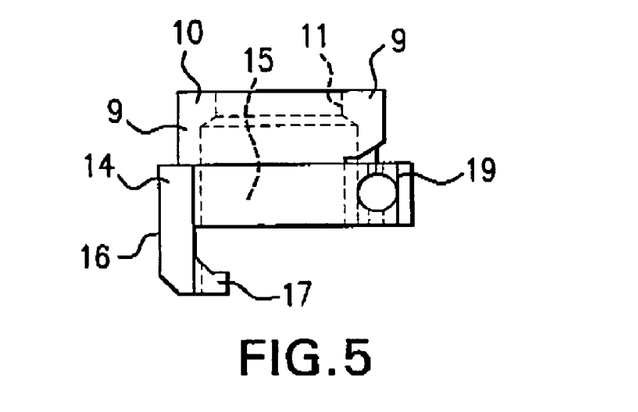
FIGS. 5 and 6 are side and plan views of a holding member body of the preferred embodiment according to the present invention.

The device 6 is attachable to, and slidable along, the guide rail 2 via the holder block 8, which is preferably configured to guide and fix the retaining device 6 on the guide rail 2. The holder block 8 preferably includes a holder body that has a substantially ring-shaped guide body 9 to position the gripping mechanism 39. As shown in FIG. 5, an inwardly projecting shoulder or collar 10 at one end of the guide body 9 forms an inner guiding bore 11 in which is guided a thrust sleeve 12. FIG. 1a shows an end position of the thrust sleeve 12 in the guiding bore 11. An outer shoulder 13, as shown in FIG. 4, preferably configured as a collar, at one end of the thrust sleeve 12 abuts against the inwardly projecting shoulder or collar 10 of the guide body 9 at this end of the thrust sleeve 12 during displacement of the thrust sleeve 12 in the guiding bore 11. The shoulder 13 thus limits the stroke or displacement motion of the thrust sleeve 12.

Figure 6:
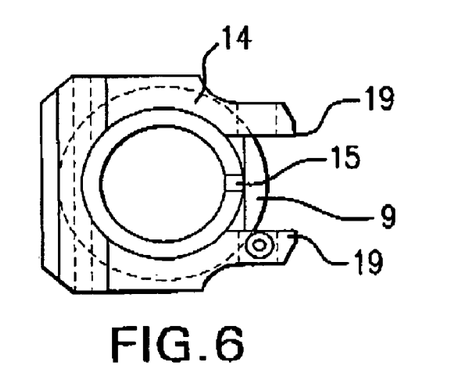

The cylindrical guide body 9, at the side or end located opposite the inwardly projecting shoulder 10, has merging therewith a bifurcated body portion 14 of the holder body, which is preferably substantially U-shaped and integrally formed with the ring-shaped guide body 9, visible in FIG. 6 for instance, preferably being of unitary construction therewith. Body portion 14 defines an opening 15 with, and the guide body 9 is preferably open to axially receive the thrust sleeve 12. The body portion 14 preferably has a clamping extension 16 thereof with an inwardly extending fixed clamping jaw 17. A pivotable clamping jaw 18 of the holding member is pivotably journalled about a pivot pin 20 whose oppositely situated ends are mounted in a clevis with side supports 19 of the body portion 14. Preferably, a set screw 32 secures the pivot pin 20 pin in a bore 25, shown in FIGS. 1a and 3, that extends through the jaw 18. The set screw 32 is screwed into a corresponding threaded bore of one of the side supports 19 and projects into a corresponding transverse bore or borehole provided in the pivot pin 20.

Figure 3:
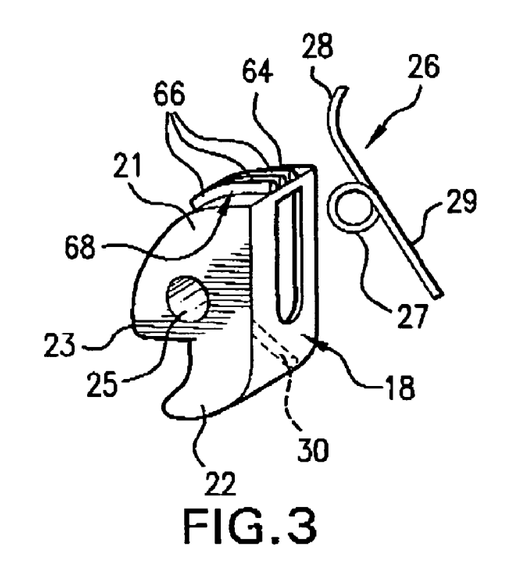
FIG. 3 is a perspective of a jaw of the preferred embodiment according to the present invention.

As shown in FIG. 3, the jaw 18 comprises two arms 21,22 extending at different angles from the axis of bore 25 and connected to each other by a connection body portion 23. The entire pivotable clamping jaw 18 is preferably of unitary construction and has a centrally disposed recess 24 (see FIG. 1a) to receive a spring 26 that is mounted on the pivot pin 20. A spring 26, such as a hairpin spring or other suitable spring, is disposed in the recess 24, preferably with the pivot pin 20 (see FIG. 1a) extending through the coiled portion 27 of the spring 26. Another bore 30 is open to the recess 24 and preferably receives a tensioning or biasing arm 29 of the spring 26 (see. FIG. 1a). The other biasing or tensioning arm 28 of the spring 26 contacts a bottom surface 31 of the thrust sleeve 12.

Spring 26 thus biases the jaw 18 to pivot in a direction opposite direction B This pivotal motion in direction B is effected by an axial force A that acts upon the arm 21 of jaw 18. Axial force A causes the pivotable clamping jaw 18 to swivel in the clockwise direction B, as depicted in FIG. 1a, towards a clamping position, in which the jaw and the fixed clamping jaw 17 cooperatively clamp the guide rail 2 disposed in clamping space 62 between the clamping jaws 17 and 18.

Inclined faces at the inside of both clamping jaws 17 and 18 of the holder block 8 preferably press against the vertical faces or surfaces 4 of the guide rail 2 during tensioning or tightening of the retaining device 6. Additionally, the configuration of the inner surfaces of the clamping jaws 17 and 18 enables the use the same holder block 8 for mounting to many differently shaped guide rails 2 or other structures. For instance, guide rails 2 standards can vary between countries. The fixed clamping jaw 17 is preferably substantially hook-shaped, enabling it to hook over and engage behind the horizontal surface 3 of the guide rail 2. Consequently, the retaining device 6 as a whole can remain hanging, suspended on the guide rail 2, even when the pivotable clamping jaw 18 is not clampingly engaging the guide rail 2, thus minimizing or avoiding an unintentional dropping of the device onto the floor.

Figure 2:
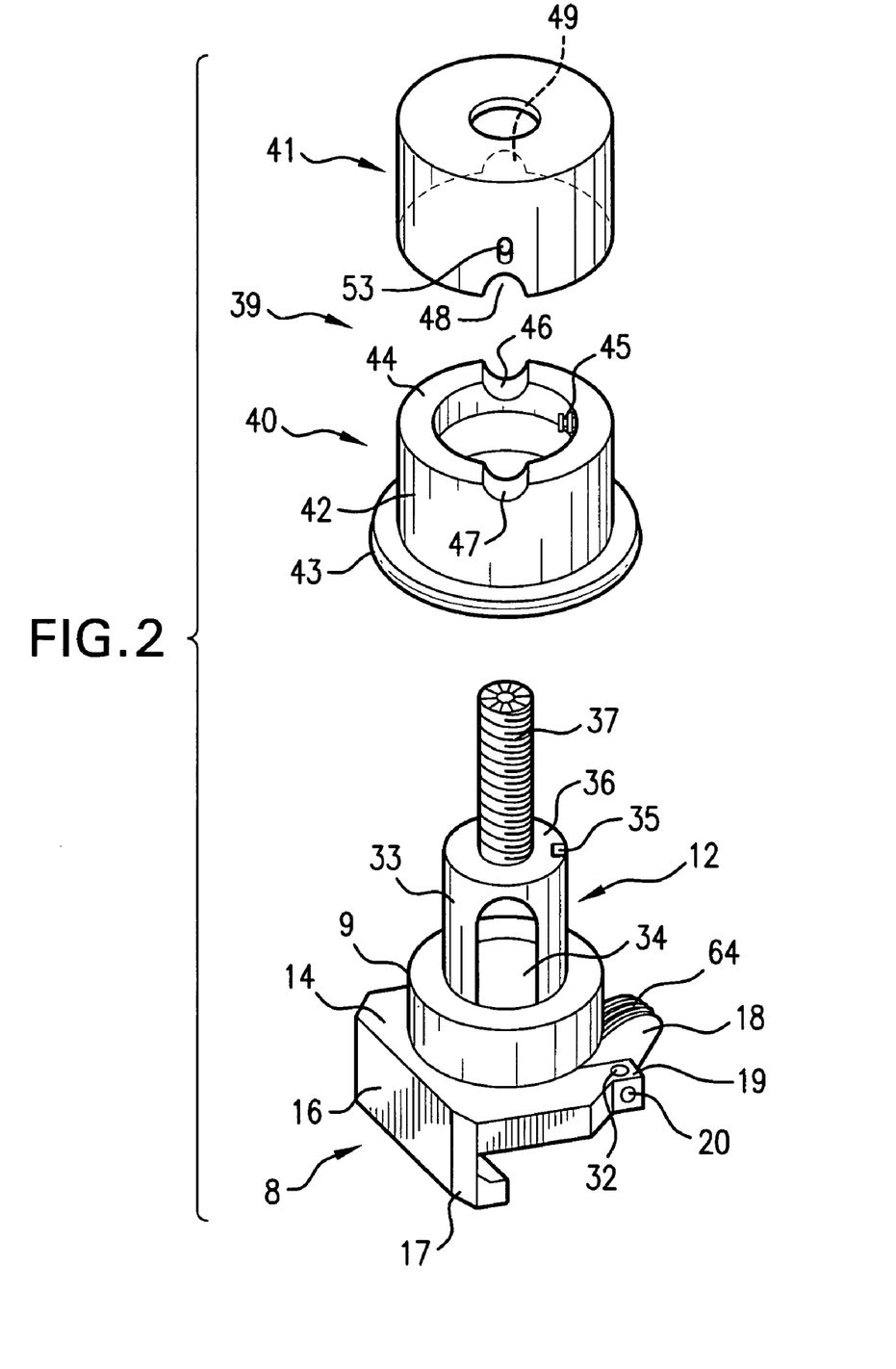
FIG. 2 is an exploded view of holding and gripping members thereof according to the present invention.

As best recognized by referring to FIGS. 1a, 2, and 4, the thrust sleeve member 12 has a substantially cylindrical portion 33 provided with an elongated hole or opening 34. The cylindrical portion 33 further includes a longitudinal groove 35. On a top surface 36 of the thrust sleeve 12, located opposite the bottom surface 31 thereof, a threaded spindle 37, such as a bolt, is axially attached to the thrust sleeve 12. Screwed onto the bolt 37 is a tightening nut, such as a butterfly or wing nut 38, which is configured as a manually operably actuating member to tighten or loosen the retaining device 6 from the guide rail 2 on the operating table 1. A radially enlarged cap 38' on the threaded spindle 37 can be included to prevent disengagement of the wing nut 38 from the threaded bolt 37.

The thrust sleeve 12 coacts with a gripping member 39. The gripping mechanism 39 comprises an inner gripping portion 40 and an outer gripping portion 41. The inner gripping portion 40 has a cylindrical or ring-shaped portion 42 terminating in an outwardly projecting flange 43, preferably at an end thereof, whereas the other end is provided with an inwardly projecting flange 44, the inside diameter of which corresponds to the outside diameter of the cylindrical portion 33 of the thrust sleeve 12. The inwardly projecting flange 44 is further provided with a guide pin or projection 45, which radially extends inwardly, projecting into the longitudinal groove 35 of the thrust sleeve member 12. The inner diameter of the cylindrical portion 42 corresponds to the outside diameter of the cylindrical guide body 9.

With reference to FIG. 1a, the inwardly projecting flange 44 has on its outer or right-hand side thereof two diametrically opposed and coaxially arranged recesses 46 and 47, each having a substantially semi-cylindrical or semi-circular cross-section. Together with correspondingly shaped semi-cylindrical or semi-circular recesses 48 and 49 provided in the outer or right-hand located cover-like clamping or gripping head 41, they constitute a passageway for the support rod 7. The recesses 46, 47, 48 and 49 are configured as contact surfaces for gripping the support rod 7 and can alternatively have a different shape to grip another shaped object. The passageway extends preferably substantially perpendicular to and intersects the longitudinal axis 60 of the holder block 8.

The support rod 7, also extending through the elongated hole or opening 34 of the thrust sleeve 12, has a longitudinal groove 54 into which projects a key 61, which is associated with an arresting sleeve 50 that preferably has radially external ridges or teeth 52. The arresting sleeve 50 is displaceably guided upon the support rod 7 but is substantially kept from rotating thereabout by the mated key 61 and groove 54. The teeth 52 of the arresting sleeve 50 define spaces therebetween to cooperate with a pin 53, two of which are preferably provided in the outer gripping portion 41 for selectively fixing the rotational position of the support rod 7 with respect to the gripping member 39. For example, eight, ten, or twelve spaces, or any other suitable arrangement of spaces, can be used to cooperate with pin 53 to provide sufficient rotationally fixed positions.

In operation, as shown in FIG. 1, the holder block 8 is positioned onto the guide rail 2 such that this guide rail 2 is located between the fixed clamping jaw 17 and the pivotable clamping jaw 18. The support rod 7, directly or indirectly supporting the surgical instrument 51, extends through the passageway formed by recesses 46, 47, 48 and 49 of the gripping member 39 and through the elongated opening 34 of the thrust sleeve 12. This thrust sleeve 12 is subjected to the action or force of the bent tensioning arm 28 of the spring 26. The outwardly projecting flange 43 of the inner gripping portion 40 is in abutting relationship with the arm 21 of the pivotable clamping jaw 18. This is the open or unclamped position of the retaining device 6, i.e., of each of the holder block 8, pivotable jaw 18, and gripping member 39. In this open position, the holder block 8 can slide along the guide rail 2 while the support rod 7 can elevationally slide in the gripping member 39.

Both gripping portions 40,41 bear against the inclined protruding arm 21 of the pivotable clamping jaw 18, which is retained in its open position under the action of the spring 26. The gripping member 39 together with the support rod 7 can be rotated around the guide body 9 to allow angular displacement of the support rod 7 in the direction of the double-headed arrow C in FIG. 1 about the longitudinal axis of the device 6. Preferably, this rotation is generally within a substantially vertical plane parallel to the guide rail 2 and substantially perpendicular to the threaded bolt or screw 37.

When the wing nut 38 is tightened, the inner and outer gripping portions 40, 41, which are guided against relative rotation, are pressed against one another to fixedly grip and retain the support rod 7 in the semi-circular recesses 46, 47, 48 and 49. Simultaneously, both gripping portions 40,41 are slid together along the thrust sleeve 12. The movement of the gripping portions 40,41 is possible by virtue of the provision of the elongate hole or opening 34. This movement causes the flange 43 of the inner gripping portion 40 to move in the direction of the arrow A (FIG. 1a), thereby exerting a force upon the jaw arm 21, which is thus cammed in a rotational clockwise movement in the direction of the arrow B against the action of the spring 26. The resulting pivotal motion of the jaw 18 in relation to the fixed clamping jaw 17 causes the device 6 to be firmly clamped onto the guide rail 2. In this manner, the entire retaining device 6 is fixed in a position determined by the user. Preferably only the wing nut 38 needs to be tightened to simultaneously grip and fix the support rod 7 in its desired position and to clamp the holder block 8 onto the guide rail 2. Loosening the wing nut 38 results in simultaneously loosening or releasing these parts. A sterilized hood or the like can be clamped by the pivotable clamping jaw 18 substantially without impeding the manipulation of the retaining device 6.

Loosening of the retaining device 6 is accomplished by turning the wing nut 38 in the opposite direction, thus allowing the pivotable clamping jaw 18 to pivot in the counterclockwise direction under the action of the spring 26, towards an open position, away from the closed position. The counterclockwise pivoting of the arm 21 of the pivotable clamping jaw 18 cams gripping portions 40,41 outwardly, to the right in FIG. 1a, along the cylindrical portion 33 of the thrust sleeve 12. In continuing the loosening the wing nut 38, the gripping portions 40,41 loosen their grip on the support rod 7. Since the gripping portions 40,41 are cammed together under the action of the spring 26, which can preferably be overpowered by hand, the gripping portions 40,41 can also be separated. The support rod 7 is thus released and free to move in relation to the holder block 8.

Figure 7:
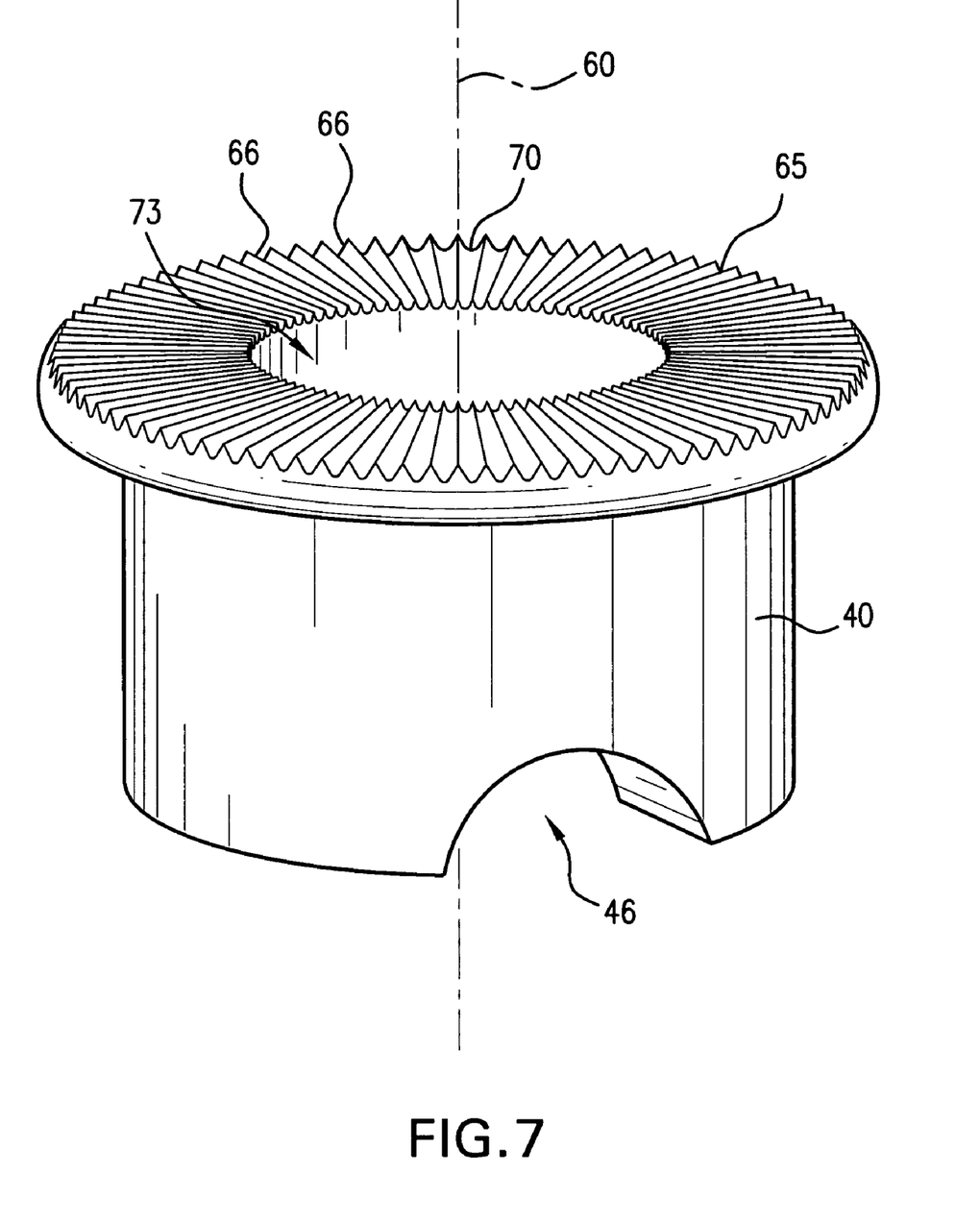
FIG. 7 is a perspective view of a portion of the gripping member of the preferred embodiment according to the present invention.

Referring to FIGS. 1a, 3, and 7, the holder block 8 and the gripping member 39 include engagement portions 64,65, which preferably comprise a plurality of teeth 66 dimensioned and pitched to meshably engage with the teeth 66 of the other engagement portion 64,65. Preferably, the teeth 66 of the engagement portion 64 of the holder block 8 extend from a contact surface 68 of the jaw arm 21. The engagement portion 64 can have a single tooth 66 (not shown) opposed to the plurality of teeth 66 of the inner gripping portion 40. Preferably, however, each of the first and second engagement portions has a plurality of intermeshing teeth. Contact surface 68 preferably has a curvature for maintaining contact with the engagement portion 65 of the inner gripping portion 40 to maintain a camming association therewith throughout pivoting of the jaw 18 between its open and clamping positions. The tooth or preferably plurality of teeth 66 on the contact surface 68 are preferably also curved to maintain the meshed engagement with the teeth 66 of the facing engagement portion 65 of the gripping portion 40 as the jaw 18 pivots. Preferably, the radial distance of the teeth 66 and contact surface 68 from the axis of the pin 20 increases in an outward direction from the longitudinal axis 60 to provide the camming association between the jaw 18 and the gripping portion 40.

While the teeth 66 on the jaw 18 are substantially parallel and are oriented in planes normal to the pivot axis of the jaw, the teeth 66 on the gripping portion 40 preferably radiate radially from the axis 60. Additionally, as visible in FIG. 1a, the base of the grooves 70 between the peaks of the engagement member 65 of gripping portion 40 are preferably slanted with respect to a plane that extends orthogonally to axis 60. The angle 72 of this slant is preferably from about 2° to 20°, and more preferably from about 5° to 15°, with the grooves 70 slanting away from the holder block 8 in a radially outward direction. This slant facilitates the camming motion with respect to the jaw 18 as the gripping portion 40 is moved longitudinally over axis 60 and the jaw 18 is pivoted about pin 20.

The engagement portion 65 of gripping member 40 preferably extends completely circumferentially around the axis 60 and central opening 73, which receives the thrust sleeve 12, so that engagement portion 65 is engagable with engagement portion 64 in substantially any relative rotational position of the holder block 8. In alternative embodiments, the engagement portion 65 can extend less than completely around the circumference of axis 60, e.g., up to about 30°, 60°, 90°, 120°, 150°, 180°, 210°, 240°, 270°, 300°, or 330° around the axis 60.

The engagement portions 64,65 are preferably capable of being in the engaged association for blocking the rotation between the holder block 8 and the gripping portion 40, both when the device 6 is fixed in the clamping position and when it is open. To disengage the engagement portions 64,65 when the device 6 is open, the jaw 18 can be manually pivoted towards the clamping position, to pivot arm 21 away from gripping member 40 against the action of spring 26. This disengagement can preferably be accomplished manually.

When the engagement portions 64, 65 are engaged with each other, the abutment between the meshed teeth 66 substantially blocks relative rotation between the holder block 8 and the gripping member 39. Preferably, this association effectively blocks the relative rotation substantially without relying on a frictional engagement between the jaw 18 and the gripping portion 40. This engagement has an improved tolerance to surface contamination that may occur during surgery, handling, or incomplete cleaning of the device 6.

Most or all of the components of the device 6 are preferably made of stainless steel or another suitable material to permit the entire, or substantially the entire device 6, to be sterilized in a conventional autoclave or other appropriate sterilizing equipment without disassembly. Preferably, the entire device is connected as a single part to minimize the risk of losing part of the device during surgery.

The term "substantially," as used herein to refer to a shape, e.g., substantially semi-cylindrical or semi-circular cross-section, is intended to include variations from the true shape that do not affect the overall function of the device.

The term "about," as used herein, should generally be understood to refer to both numbers in a range of numerals. Moreover, all numerical ranges herein should be understood to include each whole integer within the range.

While illustrative embodiments of the invention are disclosed herein, it will be appreciated that numerous modifications and other embodiments may be devised by those skilled in the art. For example, the engagement portion of the holder block 8 can also or alternatively be provided on the body portion 14 thereof. Therefore, it will be understood that the appended claims are intended to cover all such modifications and embodiments that come within the spirit and scope of the present invention.

What is claimed is:

1. A surgical tool holder comprising:
    a holding member, the holding member comprising:
        a clamping jaw having an open position, for receiving a guide rail, and a clamping position, for clamping the guide rail to mount the holding member to the guide rail, and being pivotable in a first axis, and
        a first engagement portion that is pivotable about the first axis and including a tooth, wherein the first engagement portion is associated with the clamping jaw such that pivoting of the first engagement portion causes the clamping jaw to pivot between the open and clamping positions; and
    a gripping member configured to supportingly grip a surgical tool and including a second engagement portion that is rotatable with respect to the first engagement portion about a second axis when disengaged from the first engagement portion, the second engagement portion including a plurality of teeth configured to abut and engage the first engagement portion tooth selectively in a plurality of relative rotational positions therebetween about the second axis to substantially block rotation between the holding member and the gripping member about the second axis, wherein with the teeth engaged the first and second engagement portions are operably associated such that displacement of the second engagement portion with respect to the first engagement portion causes the pivoting of the first engagement portion about the first axis to move the jaw to the clamping position while maintaining the teeth engaged,
    wherein the second engagement portion teeth define valleys therebetween that are slanted with respect to a plane that extends orthogonally to the second axis for facilitating camming the first engagement portion tooth upon the displacement of the second engagement portion teeth with respect to the first engagement portion teeth to pivot the first engagement portion.

2. The surgical tool holder of claim 1, wherein the second engagement portion extends circumferentially substantially completely around the holding member for engagement with the first engagement portion in a plurality of relative rotational positions therebetween.

3. The surgical tool holder of claim 1, wherein the jaw comprises the first engagement portion and is resiliently biased to pivot away from the clamping position, the jaw being configured to cam the second engagement portion away from the holding member while maintaining the teeth engaged.

4. The surgical tool holder of claim 1, further comprising an actuating member in threaded association with the holding and gripping members for reversibly moving the jaw to the clamping position and causing the gripping member to grip the surgical tool.

5. The surgical tool holder of claim 1, wherein the jaw includes a contact surface that comprises the first engagement portion, the contact surface being curved to maintain the engaged association of the engagement portions throughout rotation of the jaw about the second axis.

6. The surgical tool holder of claim 4, wherein the actuating member is operable to substantially simultaneously move the jaw to the clamping position and cause the gripping member to grip the surgical tool.

7. The surgical tool holder of claim 4, wherein the actuating member is in threaded association with the holding member to compress the gripping portion against the jaw to tighten the clamping of the jaw and the gripping of the gripping member.

8. The surgical tool holder of claim 1, wherein the first and second engagement portions are configured to mesh with each other in a plurality of selectable positions that are rotationally displaced from each other for adjusting an angular relationship therebetween for fine adjustment of the relative rotational orientation therebetween.

9. The surgical tool holder of claim 1, wherein the jaw and first engagement portion are fixed to each other to rotate together about the first axis.

10. The surgical tool holder of claim 1, wherein the first engagement portion tooth comprises a plurality of teeth that are meshed in meshed engagement with the second engagement portion teeth during the pivoting of the first engagement portion upon displacement of the second engagement portion with respect to the first engagement portion while maintaining engagement of the teeth.

11. The surgical tool holder of claim 10, wherein the first engagement portion teeth are sufficiently parallel to allow rotational sliding thereof against the second engagement portion teeth while maintaining the meshed engagement therewith during pivoting of the first engagement portion about the first axis.

12. The surgical tool holder of claim 11, wherein the first axis is substantially perpendicular to the second axis.

13. The surgical tool holder of claim 11, wherein the second engagement portion teeth are in camming association with the first engagement portion teeth when in meshed engagement therewith for camming the first engagement portion teeth about the first axis to move the jaw to the clamping position.

14. The surgical tool holder of claim 13, further comprising an actuating member operably associated with the holding and gripping members for compressing the gripping and clamping members towards each other for causing the gripping member to grip the surgical tool and displacing the second engagement portion against the first engagement portion for camming the first engagement portion to move the jaw to the clamping position.

15. The surgical tool holder of claim 1, wherein with the engaged teeth being operably associated such that displacement of the second engagement portion along the second axis with respect to the first engagement portion causes the pivoting of the first engagement portion about the first axis to move the jaw to the clamping position while maintaining the teeth engaged.

16. A surgical tool holder comprising:
 a holding member, the holding member comprising:
  a clamping jaw having an open position, for receiving a guide rail, and a clamping position, for clamping the guide rail to mount the holding member to the guide rail, and being pivotable in a first axis, and
  a first engagement portion that is pivotable about the first axis and including a tooth, wherein the first engagement portion is associated with the clamping jaw such that pivoting of the first engagement portion causes the clamping jaw to pivot between the open and clamping positions; and
 a gripping member configured to supportingly grip a surgical tool and including a second engagement portion that is rotatable with respect to the first engagement portion about a second axis when disengaged from the first engagement portion, the second engagement portion including a plurality of teeth configured to abut and engage the first engagement portion tooth selectively in a plurality of relative rotational positions therebetween about the second axis to substantially block rotation between the holding member and the gripping member about the second axis, wherein with the teeth engaged the first and second engagement portions are operably associated such that displacement of the second engagement portion with respect to the first engagement portion causes the pivoting of the first engagement portion about the first axis to move the jaw to the clamping position while maintaining the teeth engaged,
 wherein the second engagement portion teeth are in camming association with the first engagement portion tooth when engaged for camming the first engagement portion tooth about the first axis to move the jaw to the clamping position, the first engagement portion tooth being curved with respect to the first axis to facilitate retaining the engagement during the camming.

17. The surgical tool holder of claim 16, wherein the second engagement portion teeth define valleys therebetween that are slanted with respect to a plane that extends orthogonally to the second axis for facilitating camming the first engagement portion tooth upon the displacement of the second engagement portion teeth with respect to the first engagement portion teeth to pivot the first engagement portion.

18. The surgical tool holder of claim 17, wherein the first engagement portion tooth comprises a plurality of teeth that meshed in meshed engagement with the second engagement portion teeth during the pivoting of the first engagement portion upon displacement of the second engagement portion with respect to the first engagement portion with the teeth engaged.

* * * * *